US012691006B1

(12) United States Patent (10) Patent No.: US 12,691,006 B1
Reshamwala et al. (45) Date of Patent: Jul. 28, 2026

(54) DEVICE FOR CONTACT LENS APPLICATION ASSISTANCE

(71) Applicants: Rohan Reshamwala, Parsippany, NJ (US); John Gelles, Teaneck, NJ (US); David Slater, Lakewood, CO (US)

(72) Inventors: Rohan Reshamwala, Parsippany, NJ (US); John Gelles, Teaneck, NJ (US); David Slater, Lakewood, CO (US)

( * ) Notice: Subject to any disclaimer, the term of this patent is extended or adjusted under 35 U.S.C. 154(b) by 0 days.

(21) Appl. No.: 19/442,272

(22) Filed: Jan. 7, 2026

Related U.S. Application Data

(60) Provisional application No. 63/783,455, filed on Apr. 4, 2025.

(51) Int. Cl.
*A61F 9/00* (2006.01)
(52) U.S. Cl.
CPC .................................. *A61F 9/0061* (2013.01)
(58) Field of Classification Search
CPC .................................................... A61F 9/0061
See application file for complete search history.

(56) References Cited

U.S. PATENT DOCUMENTS 3,424,486 A * 1/1969 Clifton .................. B25B 11/007
294/187
3,897,968 A * 8/1975 Allen, Jr. .............. A61F 9/0061
294/1.2

3,922,025 A * 11/1975 Updegraff ............. A61F 9/0061
294/187
4,123,098 A * 10/1978 Shoup ................... A61F 9/0061
294/187
5,050,918 A * 9/1991 Kolze ................... A61F 9/0061
294/187
5,913,556 A * 6/1999 Perusse ................. A61F 9/0061
294/25
7,163,245 B2 1/2007 Wallock et al.
2021/0236337 A1 * 8/2021 Mahgoub ............. A61F 9/0061

* cited by examiner

*Primary Examiner* — Stephen A Vu
(74) *Attorney, Agent, or Firm* — RosserIP, LLC; Roy Rosser

(57) ABSTRACT

A system and method for assisting the application of a contact lens to a wearer's eye includes a contact lens support having a viewing tube and a light transmitting tube. A first end of the light transmitting tube is positioned proximate a distal end of the viewing tube, while a second end is exposed to a light source. Light from the source is transmitted through the tube to create a lit fixation target at the first end, ensuring proper gaze alignment during lens application. In one embodiment, the light transmitting tube is a fiber optic shaped to convey ambient room light, with perpendicular local optical axes at its ends. In another embodiment, a passive radioluminescent source, such as tritium gas exciting a phosphorescent material, provides power-independent illumination. The recessed target generates a parallax effect, restricting visibility to a narrow angle for precise gaze alignment and lens placement.

10 Claims, 3 Drawing Sheets

100

DEVICE FOR CONTACT LENS APPLICATION ASSISTANCE

CROSS REFERENCE TO RELATED APPLICATIONS

This application claims priority to U.S. provisional patent application 63/783,455 filed on Apr. 4, 2025 entitled "Device for Contact Lens Application Assistance" the contents of which are hereby fully incorporated by reference.

BACKGROUND OF THE INVENTION

The present invention relates generally to an apparatus for the insertion of contact lenses. More particularly, the present invention relates to an insertion assistance device that utilizes an illuminated fixation target to aid in optimal gaze alignment so that a wearer can easily insert a contact lens, and most particularly to a device in which the illumination may be accomplished passively.

Patients often struggle with maintaining proper eye fixation during contact lens application, leading to misalignment and difficulty applying lenses. For contact lenses that require the addition of liquid to the eye facing surface of the contact lens prior to application, such as, for instance, scleral lenses, maintaining precise eye fixation is critical to prevent air bubble formation and fluid loss. Existing devices typically require a powered source, such as a battery powered LED. Such sources have the disadvantage of adding complexity, cost, exposure of electronic components to moisture, and unanticipated depletion of battery power.

What is desirable is a passively lit target to aid stable eye fixation. The non-powered lit fixation target should preferably use ambient illumination or a radioluminescence powered source to help ensure reliability and reduce the cost of the device.

Relevant prior art includes:

U.S. Pat. No. 7,163,245 issued on Jan. 16, 2007, to Ollie Wallock et al. entitled "Contact lens insertion tool" that describes an insertion tool that includes a housing shaped to accommodate a generated light source and a power source. The generated light source is electrically connected to the power source and projects a beam of light along an axis toward a distal end of the housing. The insertion tool also includes a lens holder attached to the distal end of the housing. The lens holder has an opening that allows the beam of light to pass through the housing and lens holder. The beam of light is visible to a wearer when the lens holder is aligned with the wearer's eye. The invention uses the strategy of focusing on a target that can be clearly seen by the user to insert a lens that otherwise can't be seen by the user.

Various implementations are known in the art, but fail to address all of the problems solved by the invention described herein. Various embodiments of this invention are illustrated in the accompanying drawings and will be described in more detail below.

SUMMARY OF THE INVENTION

An inventive system and method of assisting in the application of a contact lens to a lens wearer's eye is disclosed. The device may use a passively lit target to aid stable eye fixation. The non-powered, passively lit fixation target preferably uses ambient illumination or a radioluminescence powered source to help ensure reliability and reduce the cost of the device.

Such a device may consist of a light transmitting tube situated such that a first end of the light transmitting tube may be proximate to a distal end of viewing tube in a contact lens support that allows light to pass through the contact lens support. The second end of the light transmitting tube may be exposed to a light source thereby allowing light from the light source to be transmitted through the light transmitting tube to create a lit fixation target at the first end of the light transmitting tube. By having such a lit fixation target, positioned within a user's field of view, proper gaze alignment may be ensured during lens application.

In a preferred embodiment, the light transmitting tube may be a visible light transmitting fiber optic, the contact lens support may be a commercially available product such as, but not limited to, a vented scleral cup as supplied by the DMV Corporation of Zanesville, Ohio, and the light source may be ambient room light.

Because vented scleral cups do not provide suction to hold the contact lens, they are usually held or placed in a vertical orientation during the process of insertion. Such placement may partially or fully preclude the illumination of the base of the vented scleral cup. However, illumination of the base of the cup may be required to provide a lit fixation target for the user. During standard usage of DMV Vented Scleral Cup the body, head and hands, can obstruct the flow of ambient light up through the vent which is addressed by the present invention.

In one embodiment of the present invention, the illumination of the base of the cup may be accomplished by having a suitably shaped light transmitting fiber optic to convey ambient room light to the base. This may, for instance, be accomplished by shaping the light transmitting fiber optic such that a first end has a local optical axis that is perpendicular to a second local optical axis located at a second end of the light transmitting fiber optic.

In a further embodiment of the present invention, the fixation target may be lit by a passive light source such as, but not limited to, a radioluminescence powered source that may require no charging. The radioluminescence powered source may, for instance, consist of a radioactive source coated with a phosphorescent material that may be excited by beta decay of the radioactive material. The radioactive source may, for instance, be a glass vile containing a radioactive material that emits slow electrons by beta decay such as, but not limited to, tritium gas. The phosphorescent material excited by the slow electrons to emit visible light may be a material such as, but not limited to, a copper doped zinc sulfide.

In a further embodiment of the present invention, an integrated or non-integrated powered device using a light source and a device to redirect light such as a PMMA fiber optic cable may also be used to increase the brightness.

Therefore, the present invention succeeds in conferring the following, and others not mentioned, desirable and useful benefits and objectives.

It is an object of the present invention to provide a device that enhances contact lens application by providing a lit fixation target for stable eye fixation.

It is another object of the present invention to provide a device that has a power-independent illumination system.

It is a further object of the present invention to employ a recessed light source that generates a parallax effect that restricts the target's visibility to a narrow, precisely defined angle thereby ensuring that the user's gaze is accurately aligned, facilitating precise lens placement.

BRIEF DESCRIPTION OF DRAWINGS

FIG. 4A shows a cross-sectional view of a radioluminescence powered source.

DETAILED DESCRIPTION OF THE INVENTION

Figure 1:
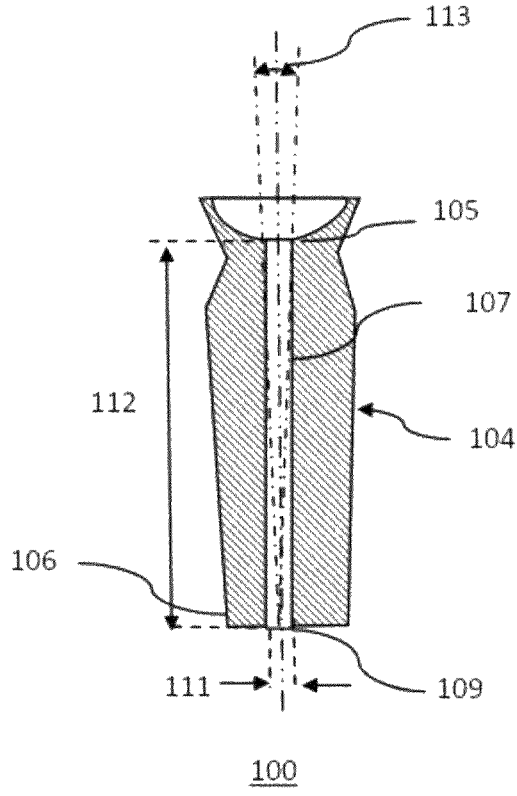
FIG. 1 shows a cross-sectional view of vented scleral cup.

The preferred embodiments of the present invention will now be described with reference to the drawings. Identical elements in the various figures are identified, as far as possible, with the same reference numerals. The embodiments that are described in detail are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a cross-sectional view 100 of vented scleral cup 104.

The vented scleral cup shown in FIG. 1 may be closely modeled on a commercially available version such as, but not limited to, that supplied by, for instance, DMV Corporation of Zanesville, Ohio.

Such vented scleral cups typically have a hollow shaft, or viewing tube 107, that runs from the base of the lens support 105 to the base or distal end 106 of the scleral cup When the base or distal end of the scleral cup is illuminated, it may provide a lit fixation target 109 visible to a user in a narrow arc 113 of parallax. Viewing such a lit fixation target may ensure stable and accurate eye alignment that may facilitate the application of a contact lens to a wearer's eye.

A typical vented scleral cup typically has an effective length 112 of about 30 mm and a width 111 of the hollow shaft, or viewing tube, of about 4 mm. This may result in an arc of parallax of about 8 degrees, which users typically find to be a usefully defined constraint for enabling stable and accurate eye alignment.

However, having such a viewing tube may preclude the lens cup from holding the lens in place by suction. The vented scleral cup is, therefore, typically used in a vertical orientation. This may preclude illumination of the base of the cup.

Figure 2:
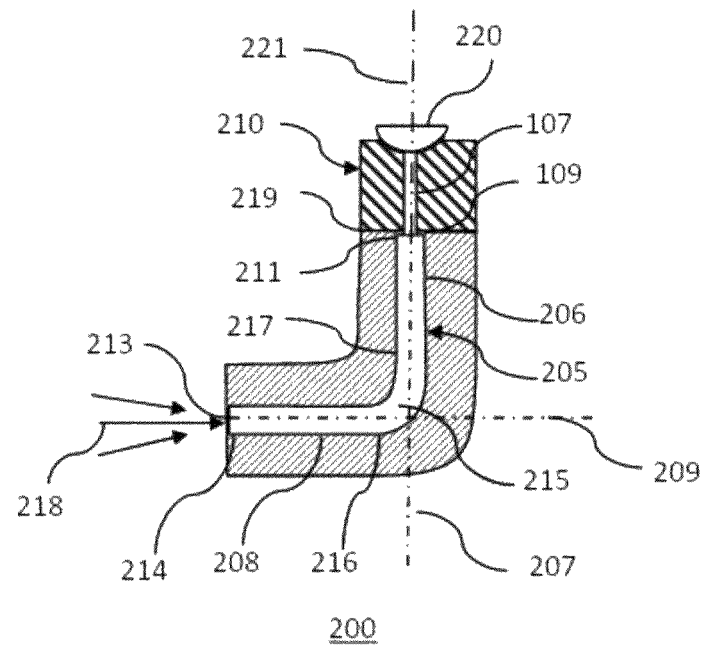
FIG. 2 shows cross-sectional view of a contact lens application assistance device of one embodiment of the present invention.

FIG. 2 shows cross-sectional view 200 of a contact lens application assistance device of one embodiment of the present invention.

The contact lens application assistance device shown in FIG. 2 may be configured so the it may be used without a contact lens 220 being held in place by suction. This may require the axis 221 of the contact lens support 210 to be placed or oriented vertically when the device is being used. The present invention may avoid such placement from partially or fully precluding the illumination of the base of the contact lens support. As shown in FIG. 2, by redirecting ambient light from a horizontal entry point up to the vertically oriented contact lens support, the device may avoid obstruction of the ambient light by, for instance, the body, head or hands.

This may, for instance, be accomplished by having a light transmitting tube 205 that may have a first straight section 206 aligned along a first local axis 207 and a second straight section 208 aligned along a second local axis 209 and wherein the first local axis and the second local axis are perpendicular to each other.

The contact lens support 210 may then be situated at a first end 211 of the first straight section of the light transmitting tube, with the contact lens support having a viewing tube 107 that allows light to pass through it.

There may also be an optical entrance aperture 213 situated at a first end 214 of the second straight section. There may also be a functional connection 215 between a second end 216 of the second straight section and a second end 217 of the first straight section such that light 218 entering the optical entrance aperture may be transmitted through the light transmitting tube to the first end of the first transmitting section, thereby forming a lit fixation target 109 at a base 219, or distal end, of the contact lens support.

When the light transmitting tube is a hollow tube, the functional connection between the first and second straight sections may, for instance, be an optical element such as, but not limited to, a mirror or a prism or a combination thereof.

However, in a preferred embodiment, the light transmitting tube may be a suitable light transmitting fiber optic, and the functional connection between the first and second straight sections of the fiber optic may consist of a suitable bend in the fiber optic.

In a further embodiment of the present invention, an integrated or non-integrated powered device using a light source and a device to redirect light such as a PMMA fiber optic cable may also be used to increase the brightness.

As shown in FIG. 2, an axis 221 of the contact lens support may be coaligned with the first local axis 207 of the first straight section 206 of the light transmitting tube 205 and, when in use, they may both be oriented vertically.

Figure 3:
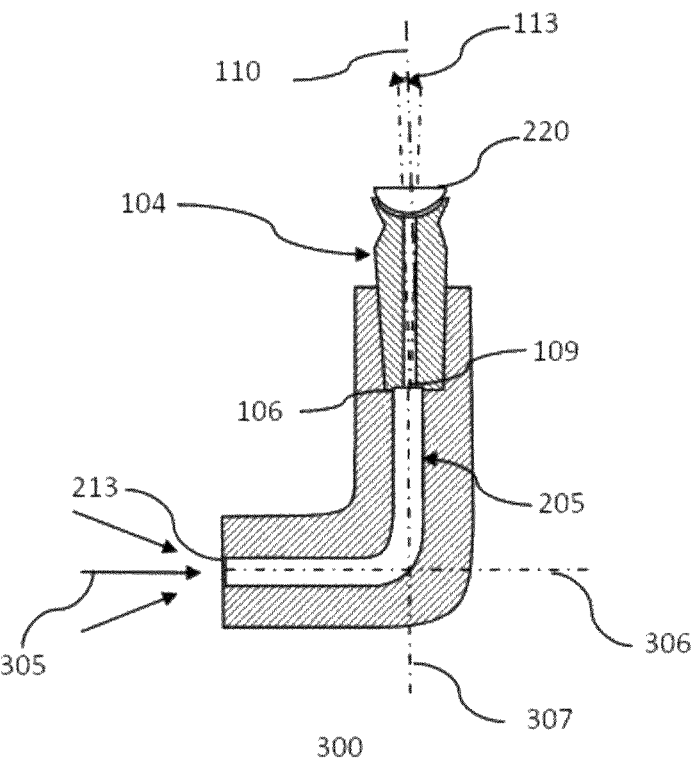
FIG. 3 shows a cross-sectional view of a contact lens application assistance device having a vented scleral cup as a contact lens support.

FIG. 3 shows a cross-sectional view 300 of a contact lens application assistance device having a vented scleral cup 104 as a contact lens support, with a contact lens 220 resting on a proximal end of the vented scleral cup.

As shown, there may be a fiber optic light transmitting tube 205 that links a light source 305 to the base or distal end 106 of the vented scleral lens, thereby created an effective lit fixation target 109 at the base of the vented scleral lens. The arc of parallax 113 that may define the viewing angle of the lit fixation target may once again be about 8 degrees.

As shown, the light transmitting fiber optic may be bent such that at an optical entrance aperture 113 of the fiber optic, a first local optical axis 306 may be horizontal, while a second local optical axis 307 at the base of the vented scleral cup may be vertical. The major axis 110 of the vented scleral cup may be co-aligned with the second local optical axis. Such an arrangement may allow the device to be placed on a flat surface, with the cup oriented vertically but the entrance aperture of the fiber being unobstructed. This may, for instance, allow the ambient light of a room to be used for illuminating the effective lit fixation target.

One of ordinary skill in the art may appreciate that the fiber may be shaped or bent to other ways, such as, but not limited to, as a U-tube, or with a 45-degree bend, and obtain a similar advantage of an unobstructed entrance aperture.

In a further embodiment of the present invention, an integrated or non-integrated powered device using a light source and a device to redirect light such as a PMMA fiber optic cable may also be used to increase the brightness.

Figure 4:
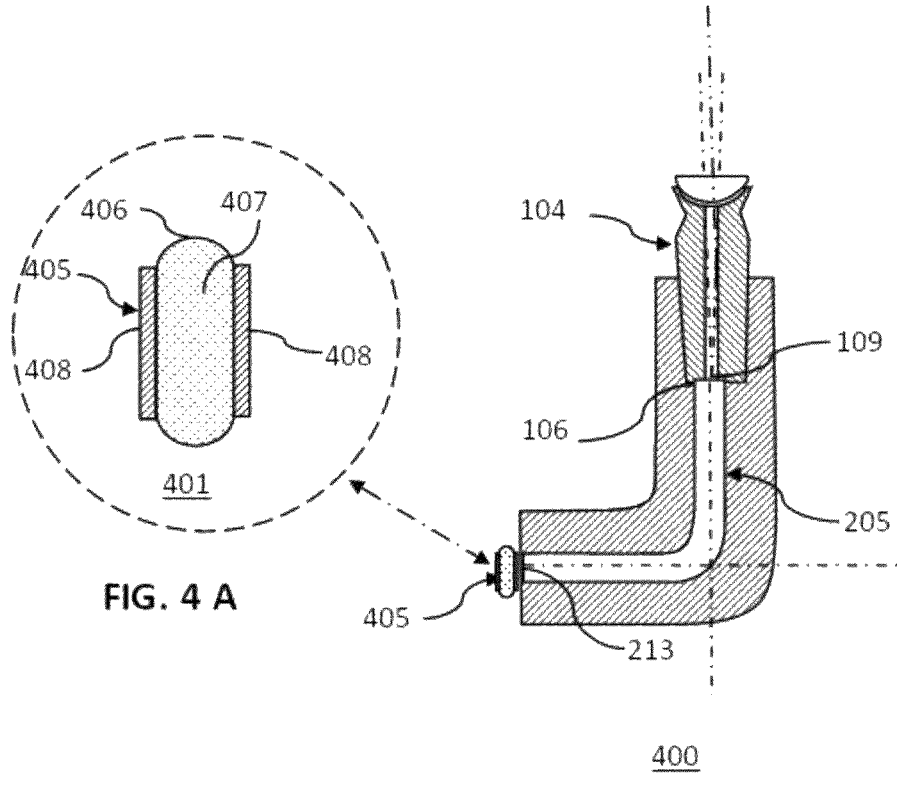
FIG. 4 shows a cross-sectional view of a contact lens application assistance device illuminated by a radioluminescence powered source.

FIG. 4 shows a cross-sectional view 400 of a contact lens application assistance device illuminated by a radioluminescence powered source 405.

As shown in FIG. 4, the radioluminescence powered source 405 may be placed at or near the optical entrance aperture 213 of the light transmitting tube 205 that may be a suitable optical fiber. A portion of the light emitted by the radioluminescence powered source 405 may then be guided by the fiber optic light transmitting tube 205 to the distal end 106 of scleral cup to form a lit fixation target 109.

FIG. 4A shows a cross-sectional view 401 of a radioluminescence powered source 405.

The radioluminescence powered source 405 may, for instance, consist of a glass vial 406 containing a radioactive substance 407 surrounded by a phosphorescent substance 408. Slow electrons emitted by the decaying radioactive substance may cause the phosphorescent substance to emit visible light. Such a process is typically referred to as radioluminescence. The radioactive substance may for instance be, but is not limited to, tritium gas. The phosphorescent substance may, for instance, be, but is not limited to, copper doped zinc sulfide.

Such a tritium/copper doped zinc sulfide radioluminescence powered source 405 may be commercially available from, for instance, the Cammenga Company LLC, of Dearborn, MI.

Although this invention has been described with a certain degree of particularity, it is to be understood that the present disclosure has been made only by way of illustration and that numerous changes in the details of construction and arrangement of parts may be resorted to without departing from the spirit and the scope of the invention.

The invention claimed is:

1. A contact lens application assistance device configured to assist a contact lens wearer in applying a contact lens onto their eye, comprising:

a light transmitting fiber optic having a first straight section aligned along a first local axis and a second straight section aligned along a second local axis and wherein said first local axis and said second local axis are perpendicular to each other;

a vented scleral cup situated at a first end of said first straight section of said light transmitting fiber optic, said vented scleral cup having a hollow viewing tube that allows light to pass through it;

an optical entrance aperture situated at a first end of said second straight section;

a functional connection between a second end of said second straight section and a second end of said first straight section such that light entering said optical entrance aperture is transmitted through said light transmitting fiber optic to said first end of said first transmitting section, thereby forming a lit fixation target at a base of said vented scleral cup, and;

a major axis of said vented scleral cup is co-aligned with said first axis of said first straight section and, when in use, both are oriented vertically.

2. The device of claim 1 wherein said light entering said optical entrance aperture comprises ambient room light.

3. The device of claim 1 wherein said light entering said optical entrance aperture comprises light emitted from a radioluminescence powered source.

4. The device of claim 3 wherein said radioluminescence powered source comprises a glass vial coated with a phosphorescent substance and containing a radioactive substance.

5. The device of claim 4 wherein said phosphorescent substance is copper doped zinc sulfide and said radioactive substance is tritium gas.

6. A method of assisting a wearer to apply a contact lens onto a lens wearer's eye, comprising:

providing a light transmitting fiber optic having a first straight section aligned along a first local axis and a second straight section aligned along a second local axis and wherein said first local axis and said second local axis are perpendicular to each other;

providing a vented scleral cup having a hollow viewing tube that allows light to pass through it;

situating said vented scleral cup at a first end of said first straight section of said light transmitting fiber optic;

providing an optical entrance aperture at a first end of said second straight section;

providing a functional connection between a second end of said second straight section and a second end of said first straight section such that light entering said optical entrance aperture is transmitted through said light transmitting fiber optic to said first end of said first transmitting section, thereby forming a lit fixation target at a base of said vented scleral cup;

co-aligning a major axis of said vented scleral cup with said first axis of said first straight section and orienting both of said axes vertically;

placing a contact lens on said vented scleral cup;

illuminating said optical entrance aperture, thereby forming said lit fixation target at said base of said vented scleral cup; and, viewing, by a user, said lit fixation target, thereby transferring said contact lens to a surface of said user's eye.

7. The method of claim 6 wherein said optical entrance aperture is illuminated using ambient room light.

8. The method of claim 6 wherein said optical entrance aperture is illuminated by light emitted from a radioluminescence powered source.

9. The method of claim 8 wherein said radioluminescence powered source comprises a glass vial coated with a phosphorescent substance and containing a radioactive substance.

10. The method of claim 9 wherein said phosphorescent substance is copper doped zinc sulfide and said radioactive substance is tritium gas.

* * * * *